US011452752B2

(12) United States Patent
Kim et al.

(10) Patent No.: US 11,452,752 B2
(45) Date of Patent: Sep. 27, 2022

(54) COMPOSITION FOR ANTIOXIDATION, ANTI-INFLAMMATION, OR OSTEOCLAST DIFFERENTIATION INHIBITION

(71) Applicant: NATURAL ENDOTECH CO., LTD., Gyeonggi-do (KR)

(72) Inventors: Jae Soo Kim, Gyeonggi-do (KR); Kwon Taek Yi, Gyeonggi-do (KR); Yong Wook Lee, Gyeonggi-do (KR)

(73) Assignee: NATURAL ENDOTECH CO., LTD., Gyeonggi-do (KR)

( * ) Notice: Subject to any disclaimer, the term of this patent is extended or adjusted under 35 U.S.C. 154(b) by 155 days.

(21) Appl. No.: 16/759,398

(22) PCT Filed: Oct. 26, 2018

(86) PCT No.: PCT/KR2018/012825
§ 371 (c)(1),
(2) Date: Apr. 27, 2020

(87) PCT Pub. No.: WO2019/083321
PCT Pub. Date: May 2, 2019

(65) Prior Publication Data
US 2020/0289597 A1    Sep. 17, 2020

(30) Foreign Application Priority Data

Oct. 27, 2017  (KR) .................. 10-2017-0141519

(51) Int. Cl.
*A61K 36/24* (2006.01)
*A61K 36/232* (2006.01)
*A61K 36/53* (2006.01)

(52) U.S. Cl.
CPC ............ *A61K 36/24* (2013.01); *A61K 36/232* (2013.01); *A61K 36/53* (2013.01); *A61K 2236/331* (2013.01); *A61K 2236/39* (2013.01)

(58) Field of Classification Search
CPC .. A61K 2300/00; A61K 36/232; A61K 36/27; A61K 36/53; A61K 36/346; A61K 2236/39; A61K 2236/331; A61K 36/24; A23L 33/105; A23L 33/15; A23L 33/16; A23V 2002/00; A23V 2200/30; A23V 2200/306; A23V 2250/156; A23V 2250/21; A23V 2250/70; A61P 13/12; A61P 15/00; A61P 15/08; A61P 15/12; A61P 17/16; A61P 19/08; A61P 1/02; A61P 25/28; A61P 43/00; A61P 5/24; A61P 5/30; A61P 9/00
See application file for complete search history.

(56) References Cited

U.S. PATENT DOCUMENTS 7,763,284 B2 *   7/2010   Kim .................... A61P 1/02
424/725

FOREIGN PATENT DOCUMENTS

| CN | 101991760 A | 3/2011 |
|---|---|---|
| CN | 102014940 A | 4/2011 |
| CN | 103906526 A | 7/2014 |
| CN | 105056190 A | 11/2015 |
| JP | 06219958 A | 8/1994 |
| KR | 10-1404168 B1 | 6/2014 |
| KR | 10-1497276 B1 | 2/2015 |
| KR | 10-2015-0045036 A | 4/2015 |
| KR | 10-2016-0144791 A | 12/2016 |

OTHER PUBLICATIONS

Kim SJ, et al "Evaluation of Estrogenic Activity of Extract from the Herbal Mixture Cynanchum wilfordii Hemsley, Phlomis umbrosa Turczaninow, and Angelica gigas Nakai", Toxicol. Res., 33(1), pp. 71-77 (Jan. 1, 2017); doi:10.5487/TR.2017.33.1.071. (Year: 2017).*
Nutraceutical Business Review "Science-backed Botanicals for Menopause Support" <URL:nutraceuticalbusinessreview.com/news/article_page/Science-backed_botanicals_for_menopause_support/140806>, Mar. 19, 2018, 3 pages (Year: 2018).*
U.S. Dept. of Health & Human Services "Bone Health and Osteoporosis: A Report of the Surgeon General", U.S. Dept. Health & Human Services, Office of the Surgeon General (Rockville, MD), 2004, Ch. 3: Diseases of Bone, (retrieved online <ncbi.nlm.nih.gov/books/NBK45506/>, WE 225 B71259 2004), pp. 40-65. (Year: 2004).*
International Search Report from corresponding PCT Application No. PCT/KR2018/012825, dated Apr. 23, 2019.
Kim, Jung Il, "Antioxdative and Antiinflammatory Activites of Cynanchi wilfordii Radix", Doctoral Thesis, Feb. 2008.
Kim, J., et al., "The Evaluation of the Effect of Herbal Extract on Osteoarthritis", Prev. Nutr. Food Sci., 2016, 21(4); pp. 310-316.
Korean Journal of Food Science and Technology vol. 47, No. 5, pp. 667-672 (2015).

(Continued)

*Primary Examiner* — Aaron J Kosar (74) *Attorney, Agent, or Firm* — Harness, Dickey & Pierce, P.L.C.

(57) ABSTRACT

The present invention relates to a composition for antioxidation, anti-inflammation, or osteoclast differentiation inhibition and a composition for arthritis treatment, each of the compositions containing a fraction of a complex extract of *Cynanchum wilfordii*, *Phlomis umbrosa*, and *Angelica gigas* as an active ingredient. The compositions of the present invention can be effectively used for osteoclast differentiation inhibition, antioxidation, or anti-inflammation, and arthritis treatment.

3 Claims, 8 Drawing Sheets

(56) References Cited

OTHER PUBLICATIONS

Office Action of KR Patent Application No. 10-2018-128930 dated Sep. 28, 2020.
Notice of Allowance KR Patent Application No. 10-20118-0128930 dated Jan. 14, 2021.
Office Action of CN Patent Application No. 201880070189.8 dated Oct. 9, 2021.

* cited by examiner

COMPOSITION FOR ANTIOXIDATION, ANTI-INFLAMMATION, OR OSTEOCLAST DIFFERENTIATION INHIBITION

CROSS-REFERENCE TO RELATED APPLICATIONS

This application is a national phase application of PCT Application No. PCT/KR2018/012825, filed on 26 Oct. 2018, which claims priority to Korean Patent Application No. 10-2017-0141519, filed on 27 Oct. 2017. The entire disclosure of the applications identified in this paragraph are incorporated herein by references.

FIELD

The present invention relates to a composition for antioxidant activity, anti-inflammatory activity, or osteoclast differentiation inhibitory activity, the composition containing, as an active ingredient, a fraction of a complex hot-water extract of *Cynanchum wilfordii*, *Phlomis umbrosa*, and *Angelica gigas*.

BACKGROUND

Osteoclasts, which are cells that reabsorb bone, are activated by a variety of in-vivo factors and maintain bones of good quality through a balance with osteoblasts. The imbalance between osteoclasts and osteoblasts causes various bone diseases, and particularly, an increase in osteoclasts causes rheumatoid arthritis, periodontitis, and the like as well as osteoporosis. Osteoclasts are derived from hematopoietic stem cells, and differentiate into mature multinucleated cells from monocytes/macrophages by macrophage colony-stimulating factor (M-CSF) and receptor activator of nuclear factor kB ligand (RANKL). The differentiation of osteoclasts occurs through a series of processes, where starting from the binding of RANK, expressed in monocytes/macrophages, and RANKL, which is a differentiation factor released from osteoblasts, tumor necrosis factor receptor-associated factor 6 (TRAF6) is recruited, and a lower pathway thereof, the phosphorylation of NF-kB, Akt, and the MAP kinases p38, JNK, and ERK induces the transcription of NFATc1, leading to the expression of osteoclast marker genes, such as tartrate-resistant acid phosphatase (TRAP), osteoclast-associated receptor (OSCAR), and cathepsin K. Therefore, the inhibition of osteoclast differentiation and the suppression of bone resorption may be important indicators in the treatment and prevention of a bone disease, such as osteoporosis.

In clinical trials, several drugs are used to treat osteoporosis, and the most commonly used drugs are bisphosphonate-based drugs. The bisphosphonate drugs are proven to have effects of lowering bone resorption and reducing the fracture incidence in osteoporosis patients by blocking osteoclast function. However, shot-term side effects, such as acute phase reaction, severe pain of the musculoskeletal system, and hypocalcemia, and long-term side effects, such as osteonecrosis of the jaw area, atrial fibrillation, and suppression of severe bone replacement were found in patients with osteoporosis who had been treated with bisphosphonate drugs, and thus the problems in osteoporosis treatment were raised. To minimize the above side effects, attempts have been recently actively made to develop medicines, which have high therapeutic effects on various bone diseases including osteoporosis while having low toxicity and side effects, by using natural materials.

However, there are no studies or reports that a complex extract of *Cynanchum wilfordii*, *Phlomis umbrosa*, and *Angelica gigas* or a fraction thereof is effective in antioxidant activity, anti-inflammatory activity through the inhibition of nitric oxide (NO) production, and osteoclast differentiation inhibitory activity.

SUMMARY

Technical Problem

The present inventors have endeavored to develop a novel substance derived from a natural material, the novel substance having antioxidant activity, anti-inflammatory activity, or osteoclast differentiation inhibitory activity. As a result, the present inventors have established that a predetermined fraction of a complex extract of *Cynanchum wilfordii*, *Phlomis umbrosa*, and *Angelica gigas* has antioxidant activity, anti-inflammatory activity, or osteoclast differentiation inhibitory activity, and thus have completed the present invention.

An aspect of the present invention is to provide a novel composition for osteoclast differentiation inhibitory activity, antioxidant activity, or anti-inflammatory activity.

Another aspect of the present invention is to provide a pharmaceutical composition for prevention and treatment of arthritis.

Still another aspect of the present invention is to provide a food composition for prevention and alleviation of arthritis.

Technical Solution

The present inventors have endeavored to develop a novel substance derived from a natural material, the novel substance having antioxidant activity, anti-inflammatory activity, or osteoclast differentiation inhibitory activity. As a result, the present inventors have established that a predetermined fraction of a complex extract of *Cynanchum wilfordii*, *Phlomis umbrosa*, and *Angelica gigas* has antioxidant activity, anti-inflammatory activity, or osteoclast differentiation inhibitory activity.

In accordance with an aspect of the present invention, there is provided a pharmaceutical composition for osteoclast differentiation inhibitory activity, antioxidant activity, or anti-inflammatory activity, the pharmaceutical composition containing at least one of ethyl acetate and butanol fractions of a complex extract of *Cynanchum wilfordii*, *Phlomis umbrosa*, and *Angelica gigas*.

In accordance with another aspect of the present invention, there is provided a pharmaceutical composition for prevention or treatment of arthritis, the pharmaceutical composition containing at least one of ethyl acetate and butanol fractions of a complex extract of *Cynanchum wilfordii*, *Phlomis umbrosa*, and *Angelica gigas*.

*Cynanchum wilfordii*, which is used in the manufacture of the complex extract of *Cynanchum wilfordii*, *Phlomis umbrosa*, and *Angelica gigas* of the present invention, is a perennial herb belonging to the family Polygonaceae with height of 1-3 m. Its roots are tuberous and thick. *Phlomis umbrosa*, which is also used in the manufacture of the above-described complex extract, is a perennial herb belonging to the family Labiatae with height of 70-150 cm. It has five thick tuberous roots. *Angelica gigas*, which is also used in the manufacture of the above-described complex extract, is a perennial herb belonging to the family Umbelliferae with height of 1-2 m. Its roots are thick and branched.

*Cynanchum wilfordii*, *Phlomis umbrosa*, and *Angelica gigas* used in the present invention may be obtained using various organs or tissues (e.g., roots, leaves, flowers, stems, fruits, and seeds) of respective plants, and the tuberous roots of *Cynanchum wilfordii*, the tuberous roots of *Phlomis umbrosa*, and the roots of *Angelica gigas* may be preferably used.

The complex extract of *Cynanchum wilfordii*, *Phlomis umbrosa*, and *Angelica gigas* of the present invention may be prepared by (i) a single extraction process in which a mixture of *Cynanchum wilfordii*, *Phlomis umbrosa*, and *Angelica gigas* is subjected to extraction with an extraction solvent or by (ii) a manner in which extracts of the single components *Cynanchum wilfordii*, *Phlomis umbrosa*, and *Angelica gigas* are separately prepared and then the extracts of the three components are mixed.

According to an embodiment of the present invention, the mixing weight ratio (w/w/w) of *Cynanchum wilfordii*, *Phlomis umbrosa*, and *Angelica gigas* in the complex extract of the present invention is 0.5-2:0.5-2:0.5-2 on the basis of the weight of each of the respective components before an extraction process. In another embodiment, the mixing weight ratio (w/w/w) of *Cynanchum wilfordii*, *Phlomis umbrosa*, and *Angelica gigas* in the complex extract of the present invention is 0.8-1.5:0.8-1.5:0.8-1.5. More specifically, for example, a complex extract in which the mixing weight ratio (w/w/w) of *Cynanchum wilfordii*, *Phlomis umbrosa*, and *Angelica gigas* is 0.9-1.2:0.9-1.2:0.9-1.25 may be used. In one example of the present invention, a complex extract in which the mixing weight ratio of *Cynanchum wilfordii*, *Phlomis umbrosa*, and *Angelica gigas* was 1:1:1.08 was used, but the complex extract of the present invention may be prepared according to various mixing weight ratios of the respective raw materials, and is not limited to the weight ratio recited in the example described above.

As used herein, the term "mixing weight ratio (w/w)" refers to the weight ratio of respective components before an extraction process. For example, when the complex extract of the present invention is prepared through a single extraction process in which a mixture of *Cynanchum wilfordii*, *Phlomis umbrosa*, and *Angelica gigas* is subjected to extraction with a solvent extract, the term refers to a weight ratio of the respective single components *Cynanchum wilfordii*, *Phlomis umbrosa*, and *Angelica gigas* contained in the mixture. Alternatively, when the complex extract of the present invention is prepared in a manner in which extracts of the single components *Cynanchum wilfordii*, *Phlomis umbrosa*, and *Angelica gigas* are separately prepared and then the extracts of the three components are mixed, the term refers to a weight ratio of "single component-based weights", each of which is calculated by the following calculation formula.

Single component-based weight=amount of single component used in preparation of single extract×(volume of single extract used in preparation of complex extract/volume of finally produced single extract)      [Calculation Formula]

The complex extract of *Cynanchum wilfordii*, *Phlomis umbrosa*, and *Angelica gigas* may be obtained using various extraction solvents, for example, (a) water, (b) a C1-C4 anhydrous or hydrous lower alcohol (methanol, ethanol, propanol, butanol, etc.), (c) a mixed solvent of the lower alcohol and water, (d) acetone, (e) ethyl acetate, (f) chloroform, (g) 1,3-butylene glycol, and (h) butyl acetate. In an embodiment of the present invention, the complex extract of the present invention is obtained using water as an extraction solvent. Meanwhile, it would be obvious that an extract showing substantially the same effect as the extract of the present invention can be obtained using not only the above extraction solvent but also another extraction solvent.

The extract of the present invention includes extracts obtained by common purification processes as well as extracts obtained by using the above-described extraction solvents. For example, the extract of the present invention also includes active fractions obtained through various purification methods that are additionally carried out, such as separation using an ultrafiltration membrane having a predetermined molecular weight cut-off and separation by various types of chromatography (manufactured for separation according to size, charge, hydrophobicity, or hydrophilicity). More specifically, for example, an active fraction, which is obtained by filtering an extract of *Cynanchum wilfordii*, *Phlomis umbrosa*, and *Angelica gigas* through a low-molecular weight ultrafiltration membrane, may be used as the complex extract according to an embodiment of the present invention, and still more specifically, an active fraction, which is obtained by treating *Cynanchum wilfordii*, *Phlomis umbrosa*, and *Angelica gigas* with hot water and then filtering the hot-water extract through an ultrafiltration membrane with a molecular weight cut-off of 6-10 μm, and still more specifically, a molecular weight cut-off of 10 μm, may be used. The extract of the present invention may be prepared into a powder state by additional processes, such as distillation under reduced pressure and freeze-drying or spray drying.

In an embodiment of the present invention, the complex extract of *Cynanchum wilfordii*, *Phlomis umbrosa*, and *Angelica gigas* is a hot-water extract. A hot-water extraction process for preparing a hot-water extract in an embodiment of the present invention is meant to encompass all of various processes generally understood by those skilled in the art, and is not particularly limited thereto. Specifically, for example, the complex extract can be prepared by carrying out an extraction process for a predetermined period of time without any particular limitation by using water of 40° C. or higher, specifically, 50° C. or higher, more specifically 60° C. or higher, still more specifically 70° C. or higher, still more specifically 80° C. or higher, and still more specifically 90° C. or higher. The complex extract can be prepared by carrying out an extraction process for 2-10 hours, and more specifically 4-8 hours. In an embodiment, the amount of the extraction solvent used in extraction may be 3-20 times (w/v), 5-20 times (w/v), 5-15 time (w/v), 7-15 times (w/v), 7-13 times (w/v), 8-13 times (w/v), or 8-12 times (w/v) the amount of the raw materials *Cynanchum wilfordii*, *Phlomis umbrosa*, and *Angelica gigas*.

In an embodiment of the present invention, each of the ethyl acetate and butanol fraction of the complex extract of *Cynanchum wilfordii*, *Phlomis umbrosa*, and *Angelica gigas*, as an active ingredient of the present invention, means a fraction obtained through a process of fractionating the complex extract of *Cynanchum wilfordii*, *Phlomis umbrosa*, and *Angelica gigas* sequentially using (1) hexane, (2) ethyl acetate, (3) butanol, and (4) water. A specific example of the fractionation process is shown in Example 2, but is not limited thereto.

In an embodiment of the present invention, a pharmaceutical composition for osteoclast differentiation inhibitory activity, antioxidant activity, or anti-inflammatory activity contains an ethyl acetate fraction of a complex extract of *Cynanchum wilfordii*, *Phlomis umbrosa*, and *Angelica gigas*.

In an embodiment of the present invention, the composition of the present invention is used for prevention or treatment of a bone disease selected from the group consisting of bone damage, osteoporosis, periodontal disease, Paget's disease, multiple myeloma, and metastatic cancer. The above-described specific diseases are associated with osteoclast differentiation, and correspond to diseases well known to be able to be prevented or treated by inhibition of osteoclast differentiation [Wagner, E. F., & Karsenty, G. (2001). Current opinion in genetics & development, 11(5), 527-532.; Durand, M. et al. (2011). Bone, 48(3), 588-596.; Bartold, P. M. et al. (2010). Periodontology 2000, 53(1), 55-69.; Zhai, Z. J. et al. (2014). British journal of pharmacology, 171(3), 663-675.; and Heymann, D. et al. (2005). Drug discovery today, 10(4), 242-247.].

In an embodiment of the present invention, the composition of the present invention is used for prevention or treatment of arthritis, and specifically, for prevention or treatment of inflammatory arthritis or degenerative arthritis. Preferably, the composition of the present invention is used for prevention or treatment of rheumatoid arthritis, ankylosing spondylitis, Reiter's syndrome, or psoriatic arthritis, which is an inflammatory disease as a kind of autoimmune disease, and more preferably rheumatoid arthritis.

The pharmaceutical composition of the present invention may contain a pharmaceutically acceptable carrier. The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, water, syrup, and mineral oil. The pharmaceutical composition of the present invention may further contain, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in *Remington's Pharmaceutical Sciences* (19th ed., 1995).

The pharmaceutical composition of the present invention may be administered orally or parenterally (e.g., intravenous administration, intraperitoneal administration, intramuscular administration, subcutaneous administration, or topical administration), and is preferably applied in the manner of an oral administration.

A suitable dose of the pharmaceutical composition of the present invention may be variously prescribed according to factors, such as a method for formulation, a manner of administration, patient's age, body weight, gender, and morbidity, a diet, a time of administration, a route of administration, an excretion rate, and response sensitivity. A general dose of the pharmaceutical composition of the present invention is within the range of 0.001-1,000 mg/kg in adults. The dose administered into the human body may be converted on the basis of animal experiments (Shin et al., J Korean Oriental Medicine 31(3):1-7, 2010).

The pharmaceutical composition of the present invention may be formulated into a unit dosage form or may be prepared in a multi-dose container by using a pharmaceutically acceptable carrier and/or excipient according to a method that can be easily implemented by a person having an ordinary skill in the art to which the present invention pertains. Here, the formulation may be in the form of a solution in an oily or aqueous medium, a suspension, a syrup, an emulsion, an extract, pulvis, a powder, granules, a tablet, or a capsule, and may further contain a dispersant or a stabilizer.

According to still another aspect of the present invention, the present invention provides a food composition for osteoclast differentiation inhibitory activity, antioxidant activity, or anti-inflammatory activity, the food composition containing at least one of ethyl acetate and butanol fractions of a complex extract of *Cynanchum wilfordii*, *Phlomis umbrosa*, and *Angelica gigas*.

According to still another aspect of the present invention, the present invention provides a food composition for prevention and alleviation of arthritis, the food composition containing at least one of ethyl acetate and butanol fractions of the complex extract of *Cynanchum wilfordii*, *Phlomis umbrosa*, and *Angelica gigas*.

When the composition of the present invention is prepared into a food composition, such a food composition contains components that are usually added in food manufacturing, for example, proteins, carbohydrates, fats, nutrients, seasonings, and flavoring agents. Examples of the above-described carbohydrates may include: typical sugars, such as, monosaccharides, for example glucose and fructose, disaccharides, for example maltose, sucrose, and oligosaccharides, and polysaccharides, for example, dextrin and cyclodextrin; and sugar alcohols, such as xylitol, sorbitol, and erythritol. Natural flavoring agents and synthetic flavoring agents may be used as the flavoring agents. For example, when the food composition of the present invention is manufactured into a drink, such a drink may further contain citric acid, liquid fructose, sugar, glucose, acetic acid, malic acid, fruit juice, or the like, in addition to the active ingredient of the present invention.

The food composition of the present invention can use the ethyl acetate and butanol fractions of the complex extract of *Cynanchum wilfordii*, *Phlomis umbrosa*, and *Angelica gigas* contained in the pharmaceutical composition according to another aspect of the present invention, as they are, and the description of overlapping contents therebetween are omitted to avoid excessive complication of the present disclosure.

In an embodiment of the present invention, the composition of the present invention is used for prevention or alleviation of a bone disease selected from the group consisting of bone damage, osteoporosis, periodontal disease, Paget's disease, multiple myeloma, and metastatic cancer.

In an embodiment of the present invention, the composition of the present invention is used for prevention or alleviation of arthritis and, specifically, for prevention or treatment of inflammatory arthritis or degenerative arthritis. Preferably, the composition of the present invention is used for prevention or treatment of rheumatoid arthritis, ankylosing spondylitis, Reiter's syndrome, or psoriatic arthritis, which is an inflammatory disease as a kind of autoimmune disease, and more preferably rheumatoid arthritis.

As used herein, the term "alleviation" refers to a mitigation of a disease state by having effects in the recovery of human normal functions or biological activity.

Advantageous Effects

Features and advantages of the present invention are summarized as follows.

(a) The present invention provides a novel composition for antioxidant activity, anti-inflammatory activity, or osteoclast differentiation inhibitory activity.

(b) The present invention provides a novel composition for alleviation, prevention, and treatment of arthritis.

(c) The use of the composition of the present invention can productively obtain an antioxidant effect, an anti-inflammatory effect, or an osteoclast differentiation inhibitory effect without side effects.

(d) The use of the composition of the present invention can effectively alleviate, prevent, and treat arthritis without side effects.

DETAILED DESCRIPTION

Hereinafter, the present invention will be described in more detail with reference to examples. These examples are only for illustrating the present invention more specifically, and it will be apparent to those skilled in the art that the scope of the present invention is not limited by these examples according to the gist of the present invention.

Examples

Example 1: Preparation of Complex Hot-Water Extract of *Cynanchum Wilfordii, Phlomis Umbrosa*, and *Angelica gigas*

The raw herbal medicines, which were prepared by separately drying the natural medicinal herbs *Cynanchum wilfordii, Phlomis umbrosa*, and *Angelica gigas* as they are and then finely cutting the medicinal herbs, were used. 125 g of *Cynanchum wilfordii*, 125 g of *Phlomis umbrosa*, and 135 g of *Angelica gigas* were mixed, and then subjected to hot-water extraction under reflux with water, of which the weight was 10 times (w/v, 1/10) the weight of the mixed medicinal herbs, for 8 hours. Thereafter, a filtrate obtained by filtration under reduced pressure using an ultrafiltration membrane having a molecular weight cut-off of 10 μm was concentrated to 20-40 Brix under reduced pressure and then freeze-dried, thereby obtaining 172 g of a powdered complex hot-water extract of *Cynanchum wilfordii, Phlomis umbrosa*, and *Angelica gigas*.

Example 2: Preparation of Water and Organic Solvent Fractions 2-1. Hexane Fraction After 100 g of the complex hot-water extract of *Cynanchum wilfordii, Phlomis umbrosa*, and *Angelica gigas*, prepared in the above step, was completely suspended in 500 mL of water, 500 mL of hexane was added and extraction was repeated four times. Then, the hexane fraction fluid was collected, and the solvent was completely removed by concentration under reduced pressure, thereby obtaining 0.5 g of a hexane fraction.

2-2. Ethyl Acetate Fraction

After 500 ml of ethyl acetate was added to the remaining layer (lower layer fluid) excluding the hexane fraction of 2-1 above, extraction was repeated four times, and then the ethyl acetate fraction fluid was collected, and the solvent was completely removed by concentration under reduced pressure, thereby obtaining 3.2 g of an ethyl acetate fraction.

2-3. Butanol Fraction

After 500 ml of butanol was added to the remaining layer (lower layer fluid) excluding the ethyl acetate fraction of 2-2 above, extraction was repeated four times, and then the butanol fraction fluid was collected, and the solvent was completely removed by concentration under reduced pressure, thereby obtaining 7.0 g of a butanol fraction.

2-4. Water Fraction

The remaining layer (lower layer fluid) excluding the butanol fraction of 2-3 above was concentrated under reduced pressure to completely remove the solvent, thereby obtaining 89.3 g of a water fraction.

Example 3: Measurement of DPPH Radical Scavenging Activity

The free radical scavenging activity, that is, antioxidant activity was measured by investigating ability to reduce or offset the free radical DPPH, that is, oxidation inhibitory activity. DPPH is a relatively stable free radical with a dark purple color, which is reduced and decolored by a sample, and thus DPPH was used to measure antioxidant activity. Specifically, 180 μL of a 100 μM DPPH solution was added to 20 μL of the complex hot-water extract of *Cynanchum wilfordii, Phlomis umbrosa*, and *Angelica gigas* and the fractions thereof, followed by incubation for 30 minutes in a dark room, and then the absorbance was measured at 517 nm to check the DPPH radical scavenging activity according to the concentration. Vitamin C was used as a positive control substance, and the free radical scavenging activity was expressed as a percentage compared with a sample non-added group.

Figure 1:
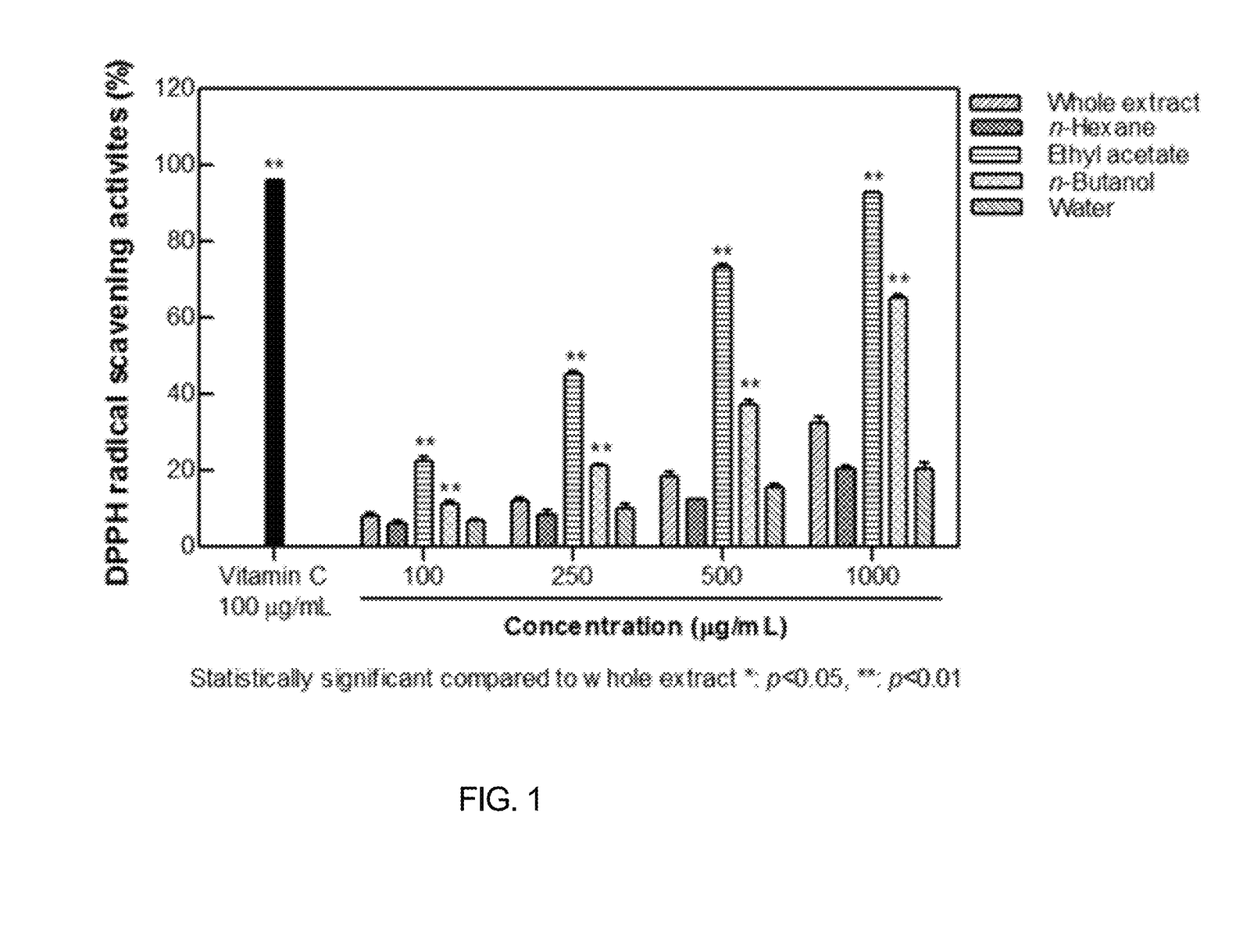
FIG. 1 shows the measurement results of DPPH radical scavenging activity according to the concentration of a complex hot-water extract of *Cynanchum wilfordii, Phlomis umbrosa*, and *Angelica gigas* and fractions thereof.

As a result, the complex hot-water extract of *Cynanchum wilfordii, Phlomis umbrosa*, and *Angelica gigas* and the fractions thereof, when compared with vitamin C, showed somewhat low DPPH radical scavenging activities, which were dependent on the concentration thereof. Especially, the ethyl acetate fraction showed high radical scavenging activity at all the concentrations when compared with the complex hot-water extract of *Cynanchum wilfordii*, *Phlomis umbrosa*, and *Angelica gigas* and the other fractions, and the ethyl acetate fraction showed DPPH radical scavenging activity similar to that of vitamin C (FIG. 1).

Example 4: Measurement of DPPH Radical Scavenging Activity

The 2,2'-azino-bis(3-ethylbenzthiazoline-6-sulfonate) (ABTS) radical scavenging activity was measured by using a method in which ABTS free radicals generated by reaction with 2,2'-azinobis(2-amidinopropane) dihydrochloride (AAPH) is removed by an antioxidant substance of a sample to result in the decoloration of blue color as a unique color of the radical. Specifically, 1.0 mM AAPH was added to 2.5 mM ABTS solution, followed by incubation in a constant-temperature water tank at 70° C. for 30 minutes.

Thereafter, 180 µL of ABTS solution was added to 20 µL of the complex hot-water extract of *Cynanchum wilfordii*, *Phlomis umbrosa*, and *Angelica gigas* and the fractions thereof, followed by incubation for 10 minutes, and then the absorbance was measured at 734 nm to check the ABTS radical scavenging activity according to the concentration. Vitamin C was used as a positive control substance, and the free radical scavenging activity was expressed as a percentage compared with a sample non-added group.

Figure 2:
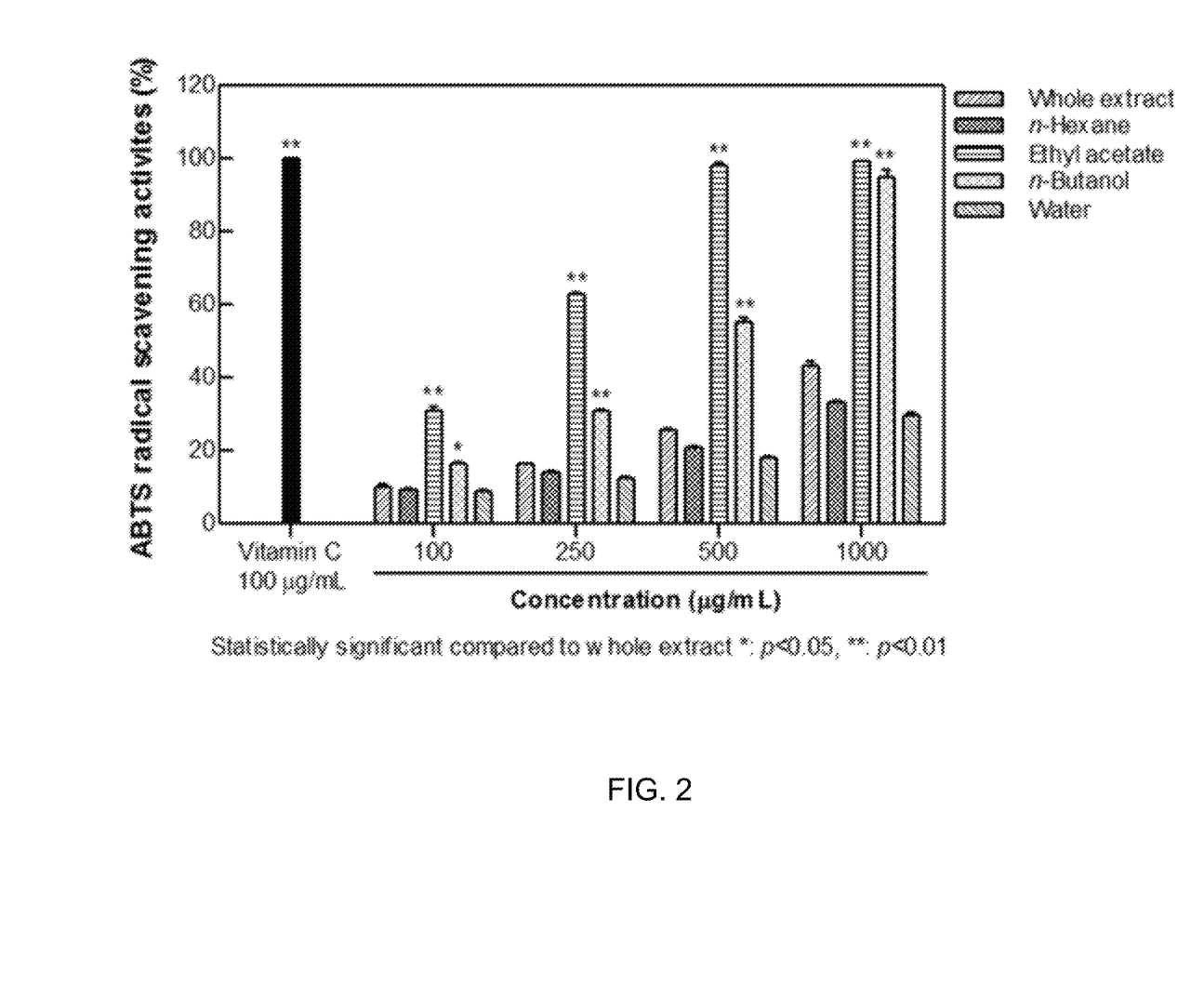
FIG. 2 shows the measurement results of ABTS radical scavenging activity according to the concentration of a complex hot-water extract of *Cynanchum wilfordii, Phlomis umbrosa*, and *Angelica gigas* and fractions thereof.

As a result, the complex hot-water extract of *Cynanchum wilfordii*, *Phlomis umbrosa*, and *Angelica gigas* and the fractions thereof, when compared with vitamin C, showed somewhat low ABTS radical scavenging activities, which were dependent on the concentration thereof. Especially, the ethyl acetate fraction showed high radical scavenging activity at all the concentrations when compared with the complex hot-water extract of *Cynanchum wilfordii*, *Phlomis umbrosa*, and *Angelica gigas* and the other fractions, and the ethyl acetate fraction at 500 and 1,000 µg/mL and the butanol fraction at 1,000 µg/mL showed ABTS radical scavenging activities similar to that of vitamin C (FIG. 2).

Example 5: Measurement of Oxygen Radical Absorbance Capacity (ORAC)

Oxygen radical absorbance capacity (ORAC) assay is a test technique for antioxidant capacity, standardized by the US department of Agriculture, and according to the assay, a buffer, a sample, and a fluorescein solution were mixed, and a free radical initiator solution was added, and then it was determined whether a fluorescence quenching reaction is inhibited by the free radical initiator solution.

Specifically, 25 µL of the complex hot-water extract of *Cynanchum wilfordii*, *Phlomis umbrosa*, and *Angelica gigas* and the fractions thereof was added in a 96-well plate, and then 150 µL of an 8.16 nM fluorescein solution was added in each well, followed by incubation at 37° C. for 10 minutes. Then, 25 µL of 153 mM AAPH solution was added in each well, followed by well mixing, and then the reduction of fluorescence was measured at 37° C. for 100 minutes at intervals of 1 minute by using a microplate reader at an excitation wavelength of 480 nm and an emission wavelength of 520 nm. Vitamin C was used as a control substance, and all the results are expressed as vitamin C equivalent (VCE).

Figure 3:
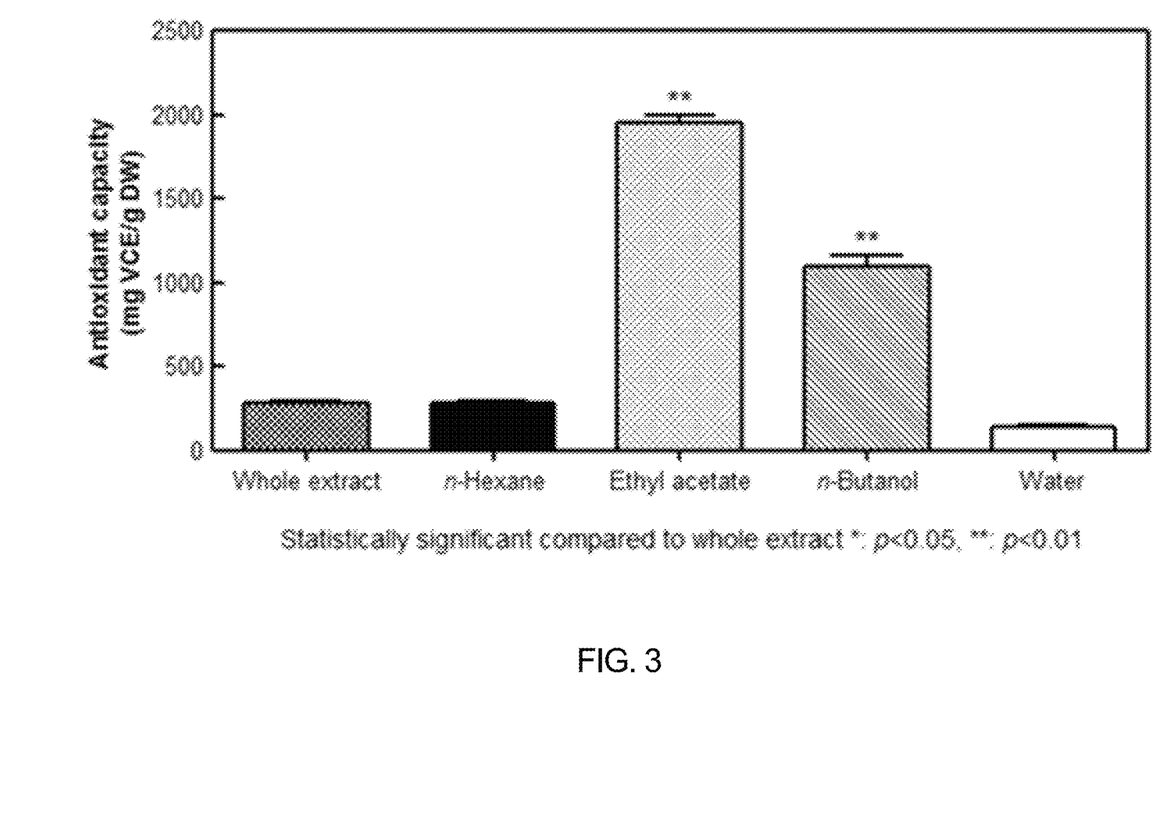
FIG. 3 shows the measurement results of oxygen radical absorbance capacities of a complex hot-water extract of *Cynanchum wilfordii, Phlomis umbrosa*, and *Angelica gigas* and fractions thereof.

As a result, the ethyl acetate fraction showed the highest ORAC value, 1954.0 mg VCE/g, and the butanol extract showed the next highest ORAC value, 1090.3 mg VCE/g (FIG. 3).

Example 6: Measurement of Anti-Inflammatory Effect Through Inhibition of Nitric Oxide (NO) Production 6-1. Confirmation of Cell Viability by Treatment with Complex Hot-Water Extract of *Cynanchum wilfordii*, *Phlomis Umbrosa*, and *Angelica gigas* and Fractions Thereof To investigate cytotoxicity of the complex hot-water extract of *Cynanchum wilfordii*, *Phlomis umbrosa*, and *Angelica gigas* and the fractions thereof, cell viability was evaluated using MTT assay before a test on nitric oxide production inhibitory ability. Specifically, RAW 264.7 cells were seeded into a 96-well plate at $5 \times 10^4$ cells/well, and then incubated at 37° C. and 5% $CO_2$ for 24 hours.

Then, the media were exchanged with cell media containing the complex hot-water extract of *Cynanchum wilfordii*, *Phlomis umbrosa*, and *Angelica gigas* and the fractions thereof diluted by concentrations were exchanged, followed by incubation for 24 hours. After the incubation, 20 µL of 3-(4,5-dimethylthiazol-2yl)-2,5-diphenyltetrazolium-bromide (MTT) solution was added in each well, followed by incubation for 4 h, and then the supernatant were removed. The formazan thus formed was dissolve in 100 µL of dimethyl sulfoxide (DMSO) solution, and the absorbance was measured at 540 nm by using a microplate reader. The cell survival rate was converted into a percentage by comparison of the measurements with the absorbance of a control group.

As a result, the complex hot-water extract of *Cynanchum wilfordii*, *Phlomis umbrosa*, and *Angelica gigas* and the fractions thereof showed cell survival rates of 95% or more at concentrations of 50, 100, 200 µg/m L, confirming little cytotoxicity.

6-2. Measurement of Nitric Oxide (NO) Production Inhibitory Effect

To investigate anti-inflammatory effects of the complex hot-water extract of *Cynanchum wilfordii*, *Phlomis umbrosa*, and *Angelica gigas* and the fractions thereof, a test on nitric oxide (NO) production inhibitory ability was conducted by GRIESS assay using RAW264.7 cells.

Specifically, RAW264.7 cells were seeded into a 96-well plate at $5 \times 10^4$ cells/well, followed by incubation for 24 hours. Then, the media were exchanged with cell media containing the complex hot-water extract of *Cynanchum wilfordii*, *Phlomis umbrosa*, and *Angelica gigas* and the fractions thereof diluted to 50, 100, and 200 µg/m L. The cells were treated together with celecoxib as a positive control, followed by pre-incubation for 3 h, and treated with 500 ng/mL of lipopolysaccharide (LPS) as a stimulus, followed by incubation for 24 hours. After the incubation, 100 µL of the supernatant was taken and transferred into a 96-well plate, and 100 µL of GRIESS solution was added, followed by incubation for 10 minutes. Thereafter, the absorbance was measured at 540 nm using a microplate reader to determine the NO production inhibitory effect.

Figure 4:
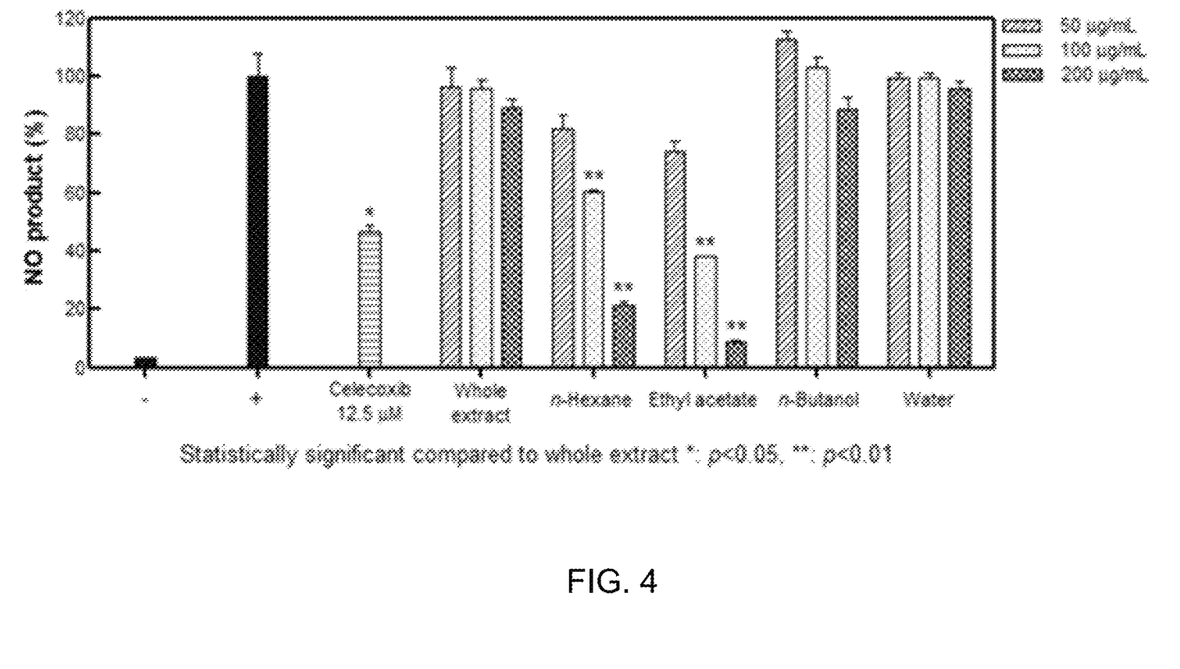
FIG. 4 shows the measurement results of nitric oxide (NO) production inhibitory activity according to the concentration of a complex hot-water extract of *Cynanchum wilfordii, Phlomis umbrosa*, and *Angelica gigas* and fractions thereof.

As a result, the NO production was reduced depending on the concentration in the hexane, ethyl acetate, and butanol fractions. Especially, the ethyl acetate fraction showed reductions in NO production to 38.2% and 8.6% at concentrations of 100 and 200 µg/mL, respectively, indicating that the NO production inhibitory effect of the ethyl acetate fraction was excellent considering 46.7% at 12.5 µM of the positive control celecoxib. In addition, the hexane fraction showed a reduction in NO production to 21.5% at a concentration of 200 μg/mL, indicating that the hexane fraction showed the next highest NO production inhibitory effect (FIG. 4).

Example 7: Measurement of Osteoclast Differentiation Inhibitory Effect 7-1. Confirmation of Cell Viability by Treatment with Complex Hot-Water Extract of *Cynanchum wilfordii*, *Phlomis Umbrosa*, and *Angelica gigas* and Fractions Thereof To investigate cytotoxicity of the complex hot-water extract of *Cynanchum wilfordii*, *Phlomis umbrosa*, and *Angelica gigas* and the fractions thereof, cell viability was evaluated using MTT assay before a test on osteoclast differentiation inhibitory effects. Specifically, RAW 264.7 cells were seeded into a 96-well plate at $5 \times 10^3$ cells/well, and then incubated at 37° C. and 5% $CO_2$ for 24 hours.

Then, the media were exchanged with cell media containing the complex hot-water extract of *Cynanchum wilfordii*, *Phlomis umbrosa*, and *Angelica gigas* and the fractions thereof diluted by concentrations and 50 ng/μL RANKL, a differentiation factor, were exchanged, followed by incubation for 24 hours. After the incubation, 20 μL of 3-(4,5-dimethylthiazol-2yl)-2,5-diphenyltetrazoliumbromide (MTT) solution was added in each well, followed by incubation for 4 hours, and then the supernatant were removed. The formazan thus formed was dissolve in 100 μL of dimethyl sulfoxide (DMSO) solution, and the absorbance was measured at 540 nm by using a microplate reader. The cell survival rate was converted into a percentage by comparison of the measurements with the absorbance of a control group.

As a result, the complex hot-water extract of *Cynanchum wilfordii*, *Phlomis umbrosa*, and *Angelica gigas* and the fractions thereof showed a cell survival rate of 93% or more at concentrations of 10, 50, 100 μg/m L, confirming little cytotoxicity.

7-2. Measurement of Osteoclast Differentiation Inhibitory Effect

To investigate the effects of the complex hot-water extract of *Cynanchum wilfordii*, *Phlomis umbrosa*, and *Angelica gigas* and the fractions thereof on osteoclast differentiation, Raw 264.7 cells were treated with RANKL to induce osteoclast differentiation, and then treated with the complex hot-water extract of *Cynanchum wilfordii*, *Phlomis umbrosa*, and *Angelica gigas* and the fractions thereof, and the differentiated osteoclasts were counted.

Specifically, RAW 264.7 cells were seeded into a 96-well plate at $5 \times 10^3$ cells/well, and then incubated at 37° C. and 5% $CO_2$ for 24 hours. Then, the media were exchanged with cell media containing 10, 50, and 100 μg/mL the complex hot-water extract of *Cynanchum wilfordii*, *Phlomis umbrosa*, and *Angelica gigas* and the fractions thereof and 50 ng/mL RANKL, and the cells were treated together with the bone resorption inhibitor alendronate as a positive control, followed by incubation for 4 days. The media were removed after the incubation, followed by washing with PBS, and then the cells were fixed and stained using a leukocyte acid phosphatase kit (Sigma). After the staining, the osteoclasts were counted using a microscope, and the osteoclast count in a sample was expressed as a percentage relative to the control.

Figure 5:
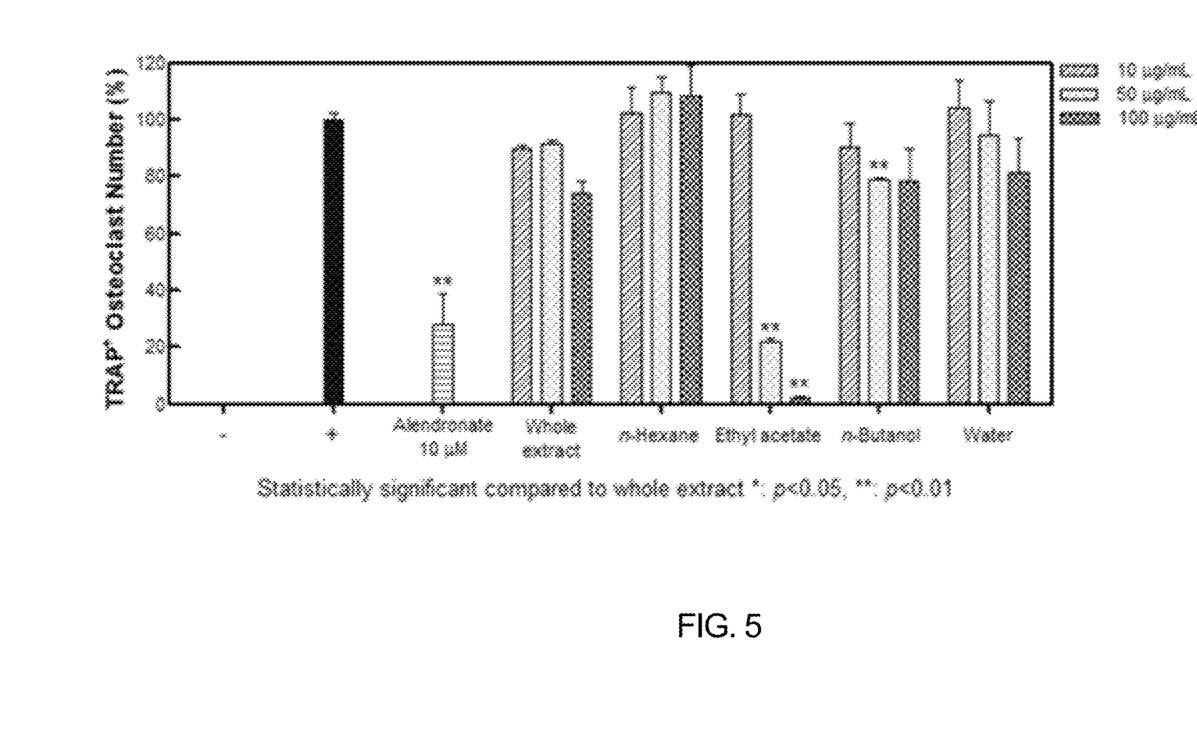
FIG. 5 shows the measurement results of osteoclast differentiation inhibitory activity according to the concentration of a complex hot-water extract of *Cynanchum wilfordii, Phlomis umbrosa*, and *Angelica gigas* and fractions thereof.
Figure 6:
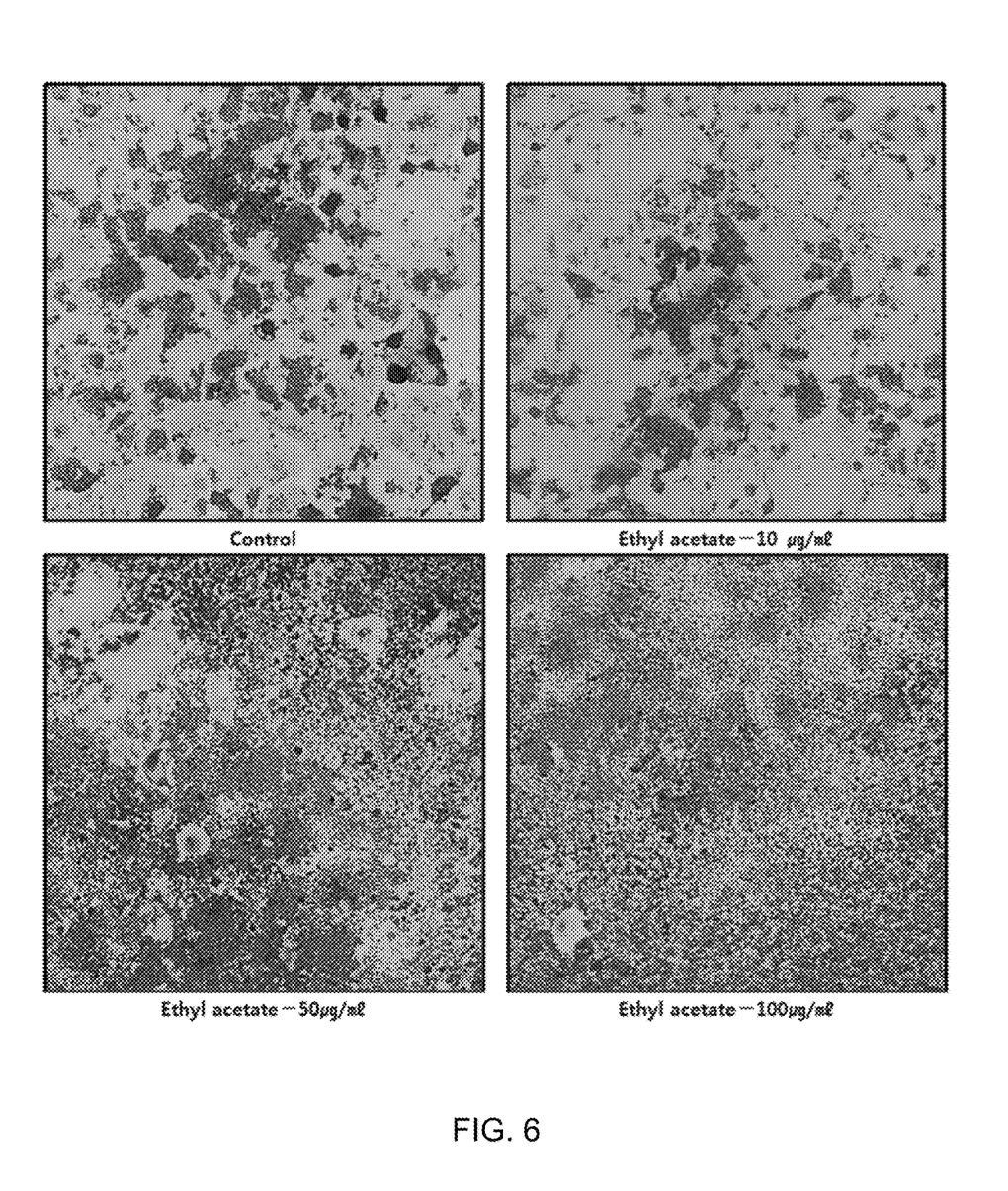
FIG. 6 illustrates images showing osteoclast differentiation inhibitory activities according to the concentration of a complex hot-water extract of *Cynanchum wilfordii, Phlomis umbrosa*, and *Angelica gigas* and fractions thereof.

As a result, the ethyl acetate fraction inhibited 78.3% and 97.7% osteoclast differentiation at concentrations of 50 and 100 μg/mL, respectively, showing higher osteoclast differentiation inhibitory effects than the complex hot-water extract of *Cynanchum wilfordii*, *Phlomis umbrosa*, and *Angelica gigas* and the other fractions, and the ethyl acetate fraction showed an osteoclast differentiation inhibitory effect higher than 72.2% at 10 mM alendronate as a positive control (FIGS. 5 and 6).

Example 8: Measurement of Prostaglandin $E_2$ ($PGE_2$) Production Inhibitory Ability To measure $PGE_2$ production inhibitory ability of the complex hot-water extract of *Cynanchum wilfordii*, *Phlomis umbrosa*, and *Angelica gigas* and the fractions thereof, an ELISA kit was used for assay. RAW 264.7 cells were seeded into a 96-well plate at $5 \times 10^4$ cells/well, and then incubated for 24 hours. Then, the media were exchanged with cell media containing the complex hot-water extract of *Cynanchum wilfordii*, *Phlomis umbrosa*, and *Angelica gigas* and the butanol and water fractions thereof diluted to 50, 100, and 200 μg/mL, and after 3 hours, the cells were treated with 1,000 ng/mL LPS, followed by incubation for 24 hours. Thereafter, the cell culture supernatant was taken, and quantified and analyzed by a method described in the user's manual of the ELISA kit.

Figure 7:
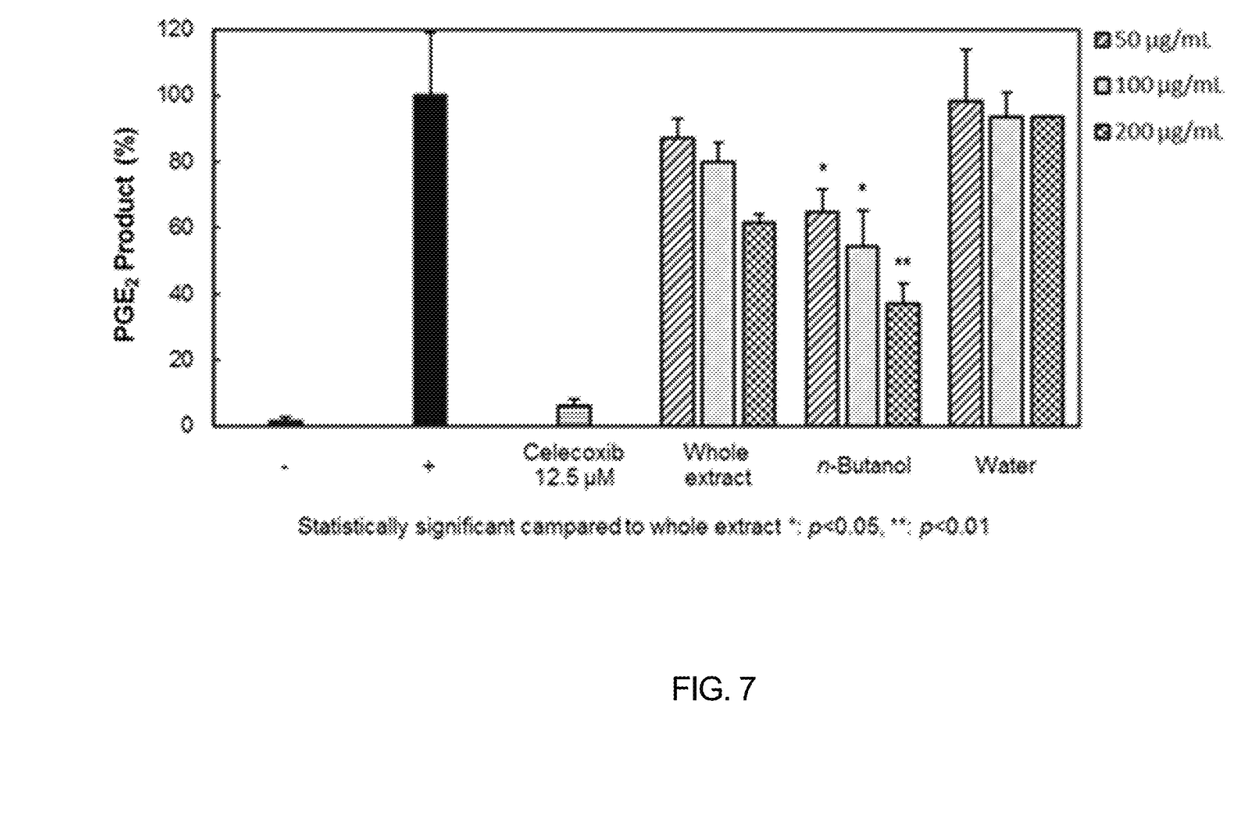
FIG. 7 shows the measurement results of prostaglandin $E_2$ ($PGE_2$) production inhibitory effect according to the concentration of a complex hot-water extract of *Cynanchum wilfordii, Phlomis umbrosa*, and *Angelica gigas* and fractions thereof.

As a result, the butanol fraction showed a reduction in $PGE_2$ production depending on the concentration thereof and, especially, showed reductions in $PGE_2$ production to 54.1% and 36.9% at concentrations of 100 and 200 μg/mL, indicating a $PGE_2$ production inhibitory effect higher than those of the complex hot-water extract of *Cynanchum wilfordii*, *Phlomis umbrosa*, and *Angelica gigas* and the water fraction thereof (FIG. 7).

Example 9: Measurement of Inflammatory Cytokine (IL-1β and IL-6) Production Inhibitory Abilities To investigate effects of the complex hot-water extract of *Cynanchum wilfordii*, *Phlomis umbrosa*, and *Angelica gigas* and the butanol and water fractions thereof on the production of inflammatory cytokines, RAW 264.7 cells were pretreated with the complex hot-water extract of *Cynanchum wilfordii*, *Phlomis umbrosa*, and *Angelica gigas* and the butanol and water fractions thereof for 3 hours before stimulation with 1.000 ng/mL LPS. After the cells were stimulated with LPS for 24 hours, tests were conducted using the cell culture supernatant according to the manual of the ELISA kit, for cytokine measurement.

Figure 8A:
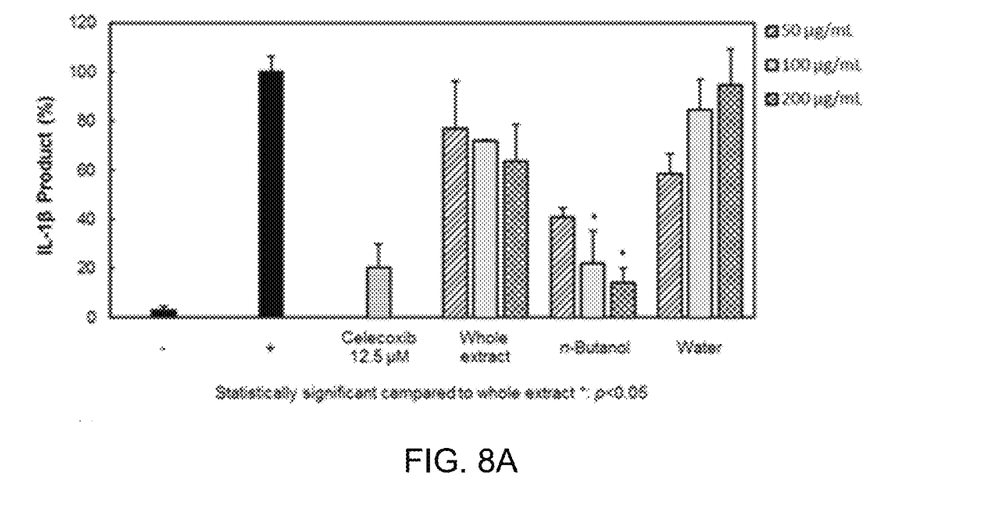
FIGS. 8A and 8B show the measurement results of inflammatory cytokine (IL-1β and IL-6) production inhibitory effects according to the concentration of a complex hot-water extract of *Cynanchum wilfordii, Phlomis umbrosa*, and *Angelica gigas* and fractions thereof.
Figure 8B:
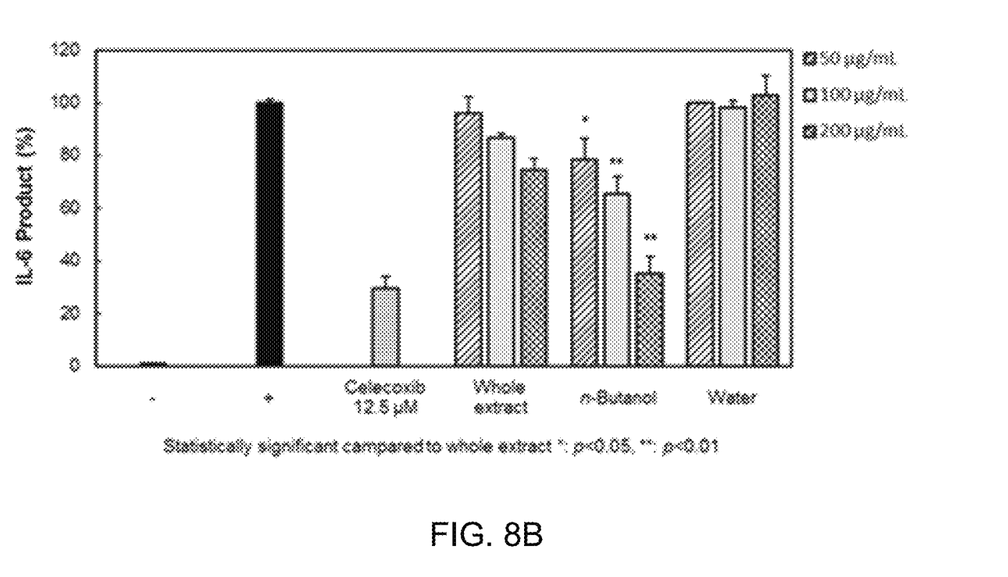

As a result, the butanol fraction showed a reduction in IL-1β production to 21.8% and 14.0% and a reduction in IL-6 production to 65.4% and 34.9% at concentrations of 100 and 200 μg/mL, indicating that the butanol fraction significantly inhibited the production of inflammatory cytokines depending on the concentration, compared with the complex hot-water extract of *Cynanchum wilfordii*, *Phlomis umbrosa*, and *Angelica gigas* and the water fraction (FIGS. 8A-8B).

What is claimed is:
1. A method for alleviation or treatment of a bone disease, the method comprising:
   administering to a subject an effective amount of a composition comprising 50 to 100 μg/mL of an ethyl acetate fraction of a complex hot-water extract of *Cynanchum wilfordii*, *Phlomis umbrosa*, and *Angelica gigas*.
2. The method of claim 1, wherein bone disease is selected from the group consisting of bone damage, osteo- porosis, periodontal disease, Paget's disease, multiple myeloma and metastatic cancer.

3. The method of claim 1, wherein the ethyl acetate fraction is obtained through a process of fractionating the complex hot-water extract of *Cynanchum wilfordii, Phlomis umbrosa*, and *Angelica gigas* sequentially using hexane, ethyl acetate, butanol and water.

* * * * *